United States Patent [19]

Domb et al.

[11] Patent Number: 4,916,204

[45] Date of Patent: Apr. 10, 1990

[54] PURE POLYANHYDRIDE FROM DICARBOXYLIC ACID AND COUPLING AGENT

[75] Inventors: Abraham J. Domb, Brookline; Robert S. Langer, Somerville; Eyal Ron, Waltham; Steven Giannos; Rohit Kothari, both of Somerville; Edith Mathiowitz, Somerville, all of Mass.

[73] Assignee: Massachusetts Institute of Technology, Cambridge, Mass.

[21] Appl. No.: 80,332

[22] Filed: Jul. 31, 1987

[51] Int. Cl.$^4$ .............................................. C08G 67/04
[52] U.S. Cl. .................................... 528/271; 528/370; 528/371
[58] Field of Search ........................ 528/271, 371, 370

[56] References Cited

U.S. PATENT DOCUMENTS 4,789,724  12/1988  Domb et al. ........................ 528/271

OTHER PUBLICATIONS

Leong et al., *Macromolecules* 20(4), 705–712 (1987).
"Morton Thiokol Inc.", Product Information for Trichloromethyl Chloroformate (Diphosgene).
Surbramanyam et al., *J. Macromol. Sci.-Chem.* A22(1), 23–31 (1985).
Cottler et al., *Chemisch.Weekblad* 63, 113–128 (1967).
Shopov et al., *Chemical Abstracts* 71, 91956w.
Ova et al., *Bulletin of the Chemical Society of Japan*.
Yoda et al., *Bull. Chem. Soc. Jpn.* 32, 1120 (1959).

*Primary Examiner*—Harold D. Anderson
*Attorney, Agent, or Firm*—Kilpatrick & Cody

[57] ABSTRACT

A method for synthesizing polyanhydrides in solution using coupling agents and a removable acid acceptor to effect a one-step polymerization of dicarboxylic acids. As used in the method, these coupling agents include phosgene, diphosgene, and acid chlorides. Insoluble acid acceptors include insoluble polyamines and cross-linked polyamines such as polyethyleneimine and polyvinylpyridine and inorganic bases such as $K_2CO_3$, $Na_2CO_3$, $NaHCO_3$, and $CaCO_3$. The only byproduct formed is a removable hydrochloric acid-acid acceptor.

Examples are provided of the polymerization of highly pure polyanhydrides using phosgene, diphosgene or an acid chloride as the coupling agent, in combination with either an insoluble acid acceptor or a soluble acid acceptor in a solvent wherein the polymerization byproduct or polymer is insoluble.

A particularly important application of these polyanhydrides is in the formation of drug delivery devices containing bioactive compounds. The method is also useful in the polymerization of dicarboxylic acids including heat liable dipeptides of glutamic or aspartic acid.

6 Claims, 4 Drawing Sheets

PURE POLYANHYDRIDE FROM DICARBOXYLIC ACID AND COUPLING AGENT

BACKGROUND OF THE INVENTION

This invention is generally in the area of polyanhydride synthesis and is in particular a method and reagents for polymerizing extremely pure polyanhydrides using solution polymerization.

Polyanhydrides are particularly useful for biomedical applications, especially in drug delivery devices, since they are biodegradable, undergo surface erosion and have erosion rates that can be changed several thousandfold by simple changes in the choice of the monomers. However, the methods for preparing highly pure polyanhydrides frequently require a number of processing steps, involve compounds which can leave toxic residues in the polyanhydride to be used in making the drug delivery device, and yield low molecular weight polymers due to hydrolysis of the anhydride bonds during purification.

At the present time, polyanhydrides are most commonly prepared by melt polycondensation. In this method, dicarboxylic acid monomers (the diacids) are first converted to the mixed anhydride with acetic acid and then polymerized under vacuum at elevated temperatures to yield the polyhydrides. In the preferred method, the temperature is limited and a dry ice trap is used to maximize the molecular weight of the final product. Purer polymers are obtained using highly purified diacids and prepolymers. Unfortunately, due to the high temperatures, this method is limited to heat-stable monomers.

A second method for polymerizing polyanhydrides is solution polymerization. Solution polymerization appears to be the method of choice for heat sensitive monomers. A variety of solution polymerizations of polyanhydrides at ambient temperatures have been reported, for example, by Yoda, et al., *Bull. Chem. Soc. Japan* 32, 1120 (1959) and Subramanyam, et al. *Macromol. Sci. Chem.* 822 (1), 23 (1985). Since the formation of an anhydride is essentially a dehydrative coupling of two carboxyl groups, it can be effected at room temperature by a dehydrochlorination between a diacid and a dicarboxylic acid in the presence of a base to yield the polyanhydride and the base.HCl, a reaction known as a Schotten-Baumann condensation. Polymerization at low temperatures in solution is also possible using a powerful dehydrative coupling reagent.

As described by Leong, et al., in *Macromolecules* 20(4), 705 (1987), this method also has a number of limitations. Leong et al examined melt-polycondensation, dehydrochlorination, and dehydrative coupling, focusing on the use of organophosphorus catalysts in the latter. He noted a number of specific disadvantages to the methods. The molecular weight of the polymer which is produced is frequently low, for example, polyterephthalic anhydride synthesized by dehydrative coupling has a molecular weight of only about 2100. Further, there are problems with the isolation and hydrolysis of the final product. Partial hydrolysis of the diacid chloride in the presence of pyridine as an acid acceptor is one cause of low molecular weight polymers. The dehydration coupling agents may also detrimentally affect polyanhydride formation, as reported for N,N-Bis(2-oxo-3-oxazoidinyl)phosphinic chloride, phenyl N-phenylphosphoramidochloridate, dicyclohexylcarbodiimide, and chlorosulfonyl isocyanate, which yielded impure polymers of low molecular weight. Further, the final products contain polymerization byproducts such as aminehydrochloride and dehydrative agent residues which have to be removed by washing with protic solvents. The washing step may cause hydrolysis of the polymer.

It is therefore an object of the present invention to provide a method for polymerization of heat sensitive monomers including dipeptides and therapeutically active diacids.

It is another object of the present invention to provide coupling agents for use in solution polymerizations of polyanhydrides.

It is a further object of the present invention to provide a method using the coupling agents to provide a single-step polymerization method for polyanhydrides, not requiring additional steps for the removal of byproducts.

SUMMARY OF THE INVENTION

A method for synthesizing polyanhydrides in solution using coupling agents and a removable acid acceptor to effect a one-step polymerization of dicarboxylic acids. As used in the method, these coupling agents include phosgene, diphosgene, and acid chlorides. Insoluble acid acceptors include insoluble polyamines and crosslinked polyamines such as polyethyleneimine and polyvinylpyridine and inorganic bases such as $K_2CO_3$, $NA_2CO_3$, $NaHCO_3$, and $CaCO_3$. The only byproduct formed is a removable hydrochloric acid-acid acceptor.

Examples are provided of the polymerization of highly pure polyanhydrides using phosgene, diphosgene or an acid chloride as the coupling agent, in combination with either an insoluble acid acceptor or a soluble acid acceptor in a solvent wherein the polymerization byproduct or polymer is insoluble.

A particularly important application of these polyanhydrides is in the formation of drug delivery devices containing bioactive compounds. The method is also useful in the polymerization of dicarboxylic acids including heat labile dipeptides of glutamic or aspartic acid.

DETAILED DESCRIPTION OF THE INVENTION

The present invention is a one-step solution polymerization of dicarboxylic acids using a coupling agent and a removable acid acceptor to yield extremely pure polyanhydrides. There are essentially two embodiments of the invention: the first, using an insoluble acid acceptor, and the second, using a solvent system wherein the solubilities of the polyanhydride and the acid acceptor byproduct are so different that one is easily separated from the other.

Coupling agents include dehydrative agents such as phosgene and diphosgene and acid chlorides such as sebacoyl chloride. Phosgene and diphosgene are preferred over the acid chlorides since they are not incorporated into the resulting polymer. The advantage is that the coupling agent can be used to form a variety of polymers, not just a polymer containing the acid residue from the acid chloride.

In the preferred embodiment, the acid acceptor is insoluble in the reaction solution. Examples of useful insoluble acid acceptors include insoluble polyamines and crosslinked polyamines such as polyethyleneimine and poly(4-vinylpyridine) and inorganic bases such as $K_2CO_3$, $Na_2CO_3$, $NaHCO_3$, and $CaCO_3$. The latter react in solution with the acid to yield the salt, which is insoluble in organic solution, and $CO_2$.

Figure 1A:
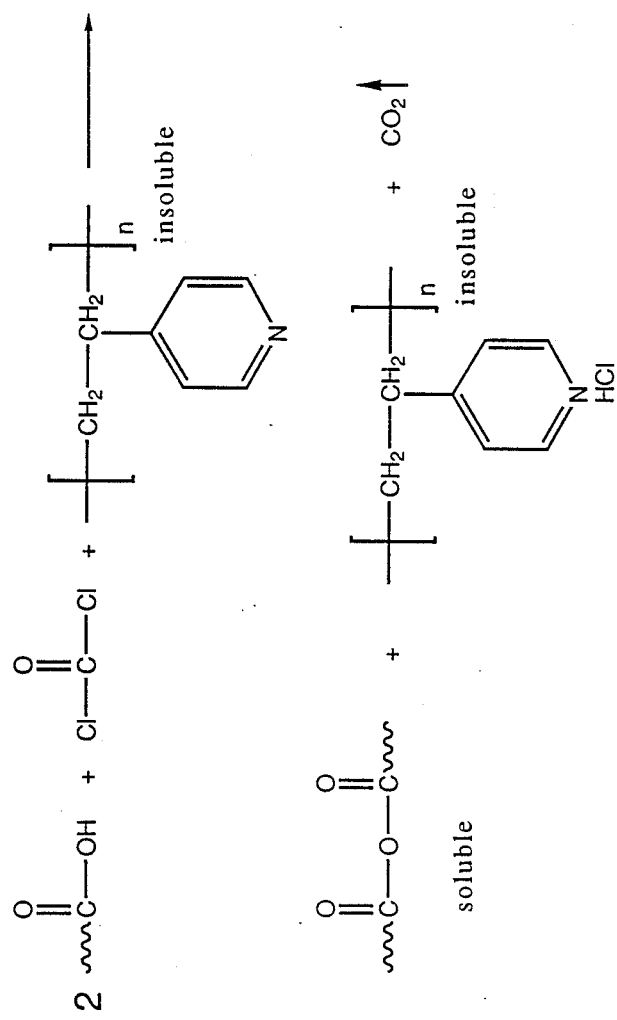
FIG. 1A is the reaction of dicarboxylic acids, a coupling agent, phosgene, and an insoluble acid acceptor, crosslinked polyvinylpyridine.
Figure 1B:
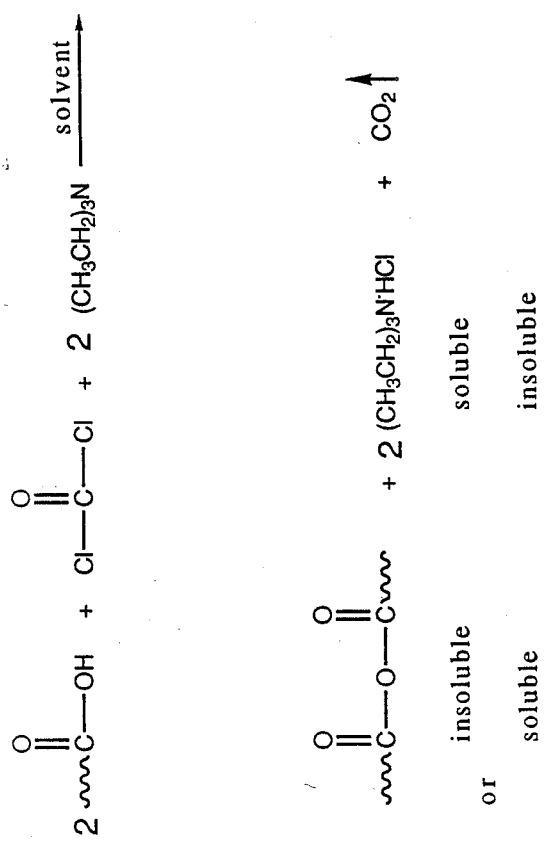
FIG. 1B is the reaction of dicarboxylic acids, a coupling agent, phosgene, and a removable acid acceptor, triethyleneamine, where either the polyanhydride product or the hydrochloric acid-acid acceptor salt is insoluble in the solvent, depending on the selection of the solvent.
Figure 1C:
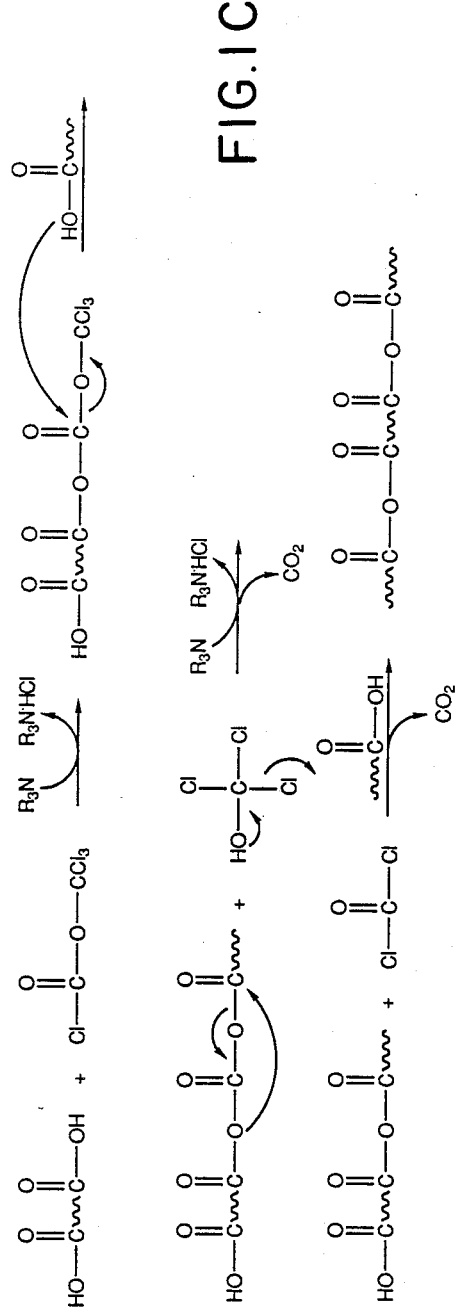
FIG. 1C is the proposed mechanism for the polymerization of polyanhydrides using diphosgene as the coupling agent in the presence of an acid acceptor.

The reactions of the diacids with the coupling agent in the presence of a removable acid acceptor, where the acid acceptor is insoluble (e.g., a crosslinked polyamine or inorganic base) is shown in FIG. 1A. The reaction using a solvent which dissolves either the polyanhydride product or the hydrochloric acid-acid acceptor salt is shown in FIG. 1B. The suggested polymerization mechanism using diphosgene as the coupling agent is shown in FIG. 1C.

Using either embodiment, where the polyanhydride in soluble and the corresponding acid acceptor-acid is insoluble or where the polymer is insoluble and the corresponding acid acceptor-acid is soluble, allows one to purify the product using a single filtration step.

Dichloroformate (phosgene) is a common reagent in organic synthesis and available commercially from suppliers such as Morton Thiokol. Trichloromethyl chloroformate (diphosgene) is a considerably less toxic phosgene dimer which is also commercially available. Other advantages include the characteristic that it is a liquid with low vapor pressure at room temperature, not requiring elaborate traps, and can be weighed directly. It has been used in a number of organic syntheses. For example, alcohols react with diphosgene to yield the corresponding trichloromethyl carbonate or, in the presence of pyridine, the chloroformate. Further reaction of the trichloromethyl carbonate with alcohol or amine produces the expected carbonate carbamate or carbonate. Isocyanates, ureas and isocyanides are prepared with either diphosgene or phosgene. N-carboxyalpha-amino acid anhydrides can be prepared from alpha amino acids using disphosgene. Diphosgene reacts with amino acids to form isocyanato acid chlorides without the need for additional reagents such as HCl, as are required in the analagous reaction with phosgene. Diphosgene has also been used to prepare phosphine dichlorides.

Despite the variety of methods these reagents have utility with, the only polyanhydrides synthesized using phosgene were low molecular weight sebacic acid oligomers, not useful for medical applications. In addition to the fact that high molecular weight polyanhydrides have not been produced using phosgene, it was not apparent until actually tested that diphosgene could be used as a coupling agent since all of the reported reactions occurred at much higher temperatures (approximately 60° C.), in contrast to the lower temperatures desired in the present method to prevent loss of bioactivity of heat sensitive compounds. Diphosgene is not as active as phosgene and there was concern that the reaction would not continue on to form the second molecule, shown in FIG. 1C. The simpler reaction with phosgene is shown in FIG. 1A and FIG. 1B.

The following nonlimiting examples further describe the present invention.

Compounds that were used are: phosgene gas (Matheson, MA), diphosgene (Martin Thiokol, MA), crosslinked poly(4-vinylpyridine) (PVP), sebacic acid (SA), sebacoyl chloride, adipic acid (AA), dodecanedioic acid (DD), terephthalic acid (TPA), 1,4 phenylenedipropionic acid (PDP), triethylamine (TEA), pyridine, tetramethylethylenediamine (TMEDA) (all from Aldrich Fine Chemicals, Milwaukee, WI). The amine bases were dried over KOH and freshly distilled prior to use. The following solvents were used: dioxane, toluene, N,N'dimethylformamide (DMF), dimethylsulfoxide (DMSO), and toluene (gold label, Aldrich, Fine Chemical, Milwaukee, WI). Chloroform and hexanes (petroleum ether) were dried over activated alumina (ICN Biomedical, Eschwege, West Germany) and distilled before use. All experiments were performed under anhydrous condition.

1,3-bis(p-carboxyphenoxy)propane was synthesized according to Conix, A., *J. Polymer Sci.* 29, 343 (1958), followed by extraction with ether prior to use. Phosgene solution was prepared by bubbling phosgene gas into toluene and adjusting the concentration to 1.0M by dilution. The concentration of this solution was determined by titration with a standard solution of 0.1N NaOH.

Infrared spectroscopy was performed on a Perkin-Elmer 1430 spectrophotometer (Perkin-Elmer, MA). Polymeric samples were film cast onto NaCl plates from a solution of the polymer in chloroform. Prepolymer samples were either pressed into KBr pellets or dispersed in nujol onto NaCl plates. The melting points of prepolymers were determined on a Fisher Johns melting point apparatus. The molecular weight of the polymers was estimated on a Perkin-Elmer GPC system (Perkin-Elmer, MA) consisting of the Series 10 pump and the 3600 Data Station with the LKB 214-rapid spectral detector at 254 nm wavelength. Samples were eluted in chloroform through two PL Gel columns (Polymer Laboratories; 100 A and 1000 A pore sizes) in series at a flow rate of 1.5 ml/min. Molecular weights of polymers were determined relative to polystyrene standards (Polysciences, PA., molecular weight ranges, 500 to 1,500,000) using CHROM 2 and GPC 4 computer programs (Perkin-Elmer, MA). Elemental analysis were performed by Galbraith Laboratories (Knoxville, TN). $^1$H NMR spectra were obtained on a Varian 250 MHz spectrophotometer using chloroform-$d_1$ as a solvent and tetramethylsilane (TMS) as an internal reference.

EXAMPLE 1

Solution Polymerization of Sebacic Acid Using Phosgene or Diphosgene as the Coupling Agent A solution of 1 eq. diacid and 2.5 to 3 eq. base in an organic solvent was prepared. Either PVP or $K_2CO_3$ was added as an insoluble acid acceptor. The resulting insoluble solid, PVP.HCl or KCl, respectively, was removed by filtration. The filtrate was added dropwise to a sufficient volume of petroleum ether to precipitate the polymer out of solution. The precipitated polymer was then isolated by filtration and dried in a vacuum oven for 24 hours at 40° C.

The results of the polymerization of sebacic acid, as a model, using either phosgene or diphosgene as coupling agents with various acid acceptors are shown in Table I. The poly(sebacic anhydride) has a weight average molecular weight up to 16,300. The results are similar for the (SA) using either phosgene or diphosgene. All of the p(SA) formed has the same melting point and IR absorbance characteristics of anhydride bonds. Insoluble polyamines, poly(4-vinylpyridine) (PVP), as well as soluble amines, TEA, pyridine, and TMEDA were used. The polymers formed with these reagents have similar molecular weights, indicating a similar role for the different amine bases as acid acceptors. Using a heterogeneous acid acceptor, PVP, does not affect the polymerization, as shown in Table I.

A non-amine heterogeneous base, $K_2CO_3$, yields a lower molecular weight polymer. This may be due to the formation of a soluble intermediate complex of acid-amine which increases the interaction with the coupling agent under homogeneous conditions. Although the PVP is insoluble in the reaction medium, it swells and forms a similar acid-PVP complex. $K_2CO_3$, however, forms a heterogeneous mixture with the acid and thus reacts slower with the coupling agents to form the polymer.

TABLE I

Polymerization of Sebacic Acid Using Phosgene and Diphosgene as Coupling Agents.[a]

| Coupling Agent | Acid Acceptor | Molecular Weight Mw | Mn | IR (cm$^{-1}$) | | MP (°C.) |
|---|---|---|---|---|---|---|
| 1. Phosgene Sol. | TEA[b] | 14800 | 6250 | 1800 | 1740 | 75–77 |
| 2. Phosgene Sol. | pyridine[b] | 13700 | 5950 | 1800 | 1735 | 76–78 |
| 3. Phosgene Sol. | TMEDA[b] | 16300 | 6600 | 1805 | 1735 | 76–78 |
| 4. Phosgene Sol. | PVP | 13950 | 5350 | 1805 | 1735 | 80–81 |
| 5. Phosgene Gas | Pyridine[b] | 14100 | 6820 | 1805 | 1735 | 75–77 |
| 6. Phosgene Gas | PVP | 13200 | 6150 | 1800 | 1735 | 79–80 |
| 7. Diphosgene | TEA[b] | 12250 | 5780 | 1805 | 1735 | 76–78 |
| 8. Diphosgene | Pyridine[b] | 14300 | 6100 | 1805 | 1740 | 75–78 |
| 9. Diphosgene | PVP | 10900 | 5300 | 1800 | 1735 | 79–80 |
| 10. Phosgene Sol. | $K_2CO_3$ | 6200 | 2700 | 1800 | 1740 | 76–78 |
| 11. Diphosgene | $K_2CO_3$ | 6900 | 3500 | 1800 | 1740 | 77–78 |

[a]Polymerization in chloroform, at 25° C., for 3 hours.
[b]Molecular weight and IR spectra were taken of the crude polymer. The IR spectra contained amine-HCl absorbance peaks at 2900–2600 cm$^{-1}$. GPC output contained an isolated peak attributed to the amine-HCl salt. Mw was determined for the polymer peak only. The melting point was determined for the pure polymer.

EXAMPLE 2

Comparison of Solution Polymerization Using Soluble and Insoluble amines

A method similar to that of Example 1 was used to polymerize the dicarboxylic acids. However, when either triethylamine (TEA) or pyridine was used as the acid acceptor, the polymerization reaction was quenched in petroleum ether and the polyanhydride, not the acid acceptor, precipitated from solution. The precipitated polymer was redissolved in chloroform and washed rapidly with a cold solution of water at pH 6. The cloroform solution was dried over $MgSO_4$ and the polymer re-precipitated by the dropwise addition of petroleum ether.

Several solvents, toluene, DMF, DMSO, and dioxane, were tested using TEA as the acid acceptor. The precipitated solids were removed by filtration. The filtrate was evaporated to dryness in vacuo at 25° C. The resulting solid was dissolved in chloroform, the polymer precipitated out by slow addition into petroleum ether, the precipitated polymer isolated by filtration and washed with diethyl ether to remove any traces of phosgene or diphogene. The composition, yield and melting points of the products formed with the various monomers and solvent mixtures are shown in Table II.

TABLE II

Solution Polymerization of Diacids in Various Solvents.

| Monomer[f] | Solvent | Analysis of Solution[a] | Analysis of Solid[b] | Yield[c] (%) | mp[b] (°C.) |
|---|---|---|---|---|---|
| 1. SA | Chloroform[e] | pSA/TEA.HCl | — | [d] | |
| 2. | Toluene[e] | pSA | pSA + TEA.HCl | 20 | 78–79 |
| 3. | N,N'-Dimethylformamide | pSA | TEA.HCl | 100 | 80–81 |
| 4. | Dimethylsulfoxide | — | — | — | — |
| 5. | Pyridine | pSA/TEA.HCl | — | [d] | |
| 6. | Dioxane | pSA/TEA.HCl | TEA.HCl | [d] | — |
| 7. CPP | Chloroform | TEA.HCl | pCPP | 100 | 265 |
| 8. TPA | Chloroform | TEA.HCl | pTPA | 100 | >300 |

[a]The solvent was evaporated and the residue was analyzed.
[b]Analysis of the precipitated solid.
[c]Pure polymer.
[d]Yield cannot be determined due to the presence of TEA.HCl.
[e]Polymerized using either diphosgene or sebacoyl chloride as coupling agents.
[f]SA is sebacic acid, CPP is 1,3-bis(p-carboxyphenoxy)propane, TPA is Terephthalic acid.

The use of a solvent system wherein the polymer is in one reaction phase (either as a precipitate or in solution), and the acid acceptor-hydrochloride acid complex is in a second phase, complementary to the polymer, is an alternative to the use of an insoluble acid acceptor. Table II describes polymerization of SA in several solvents with TEA as an acid acceptor. Polyanhydrides were obtained in good yield in toluene and in DMF. TEA in toluene or DMF is complementary to the use of PVP in chloroform. In both approaches, the p(SA) is soluble in the reaction media. The insoluble hydrochloric acid-acid acceptor complex, whether an insoluble amine, PVP.HCl, or TEA.HCl salt, is removed by filtration, leaving a polymer of greater than 99.7% purity with no need for further purification.

EXAMPLE 3

Solution Polymerization comparing an Acid Chloride as the Coupling Agent with Phosgene and Diphosgene as the Coupling Agent Solution polymerization was performed as before, using either phosgene, diphosgene or an acid chloride as the coupling agent and an acid acceptor. Reactions between sebacic acid (1 eq.) and sebacoyl chloride (1 eq.) were performed in chloroform and toluene in the presence of either PVP (insoluble) or TEA (soluble).

In a typical polymerization, 0.5 g (0.5 eq.) disphosgene was added dropwise into a stirring mixture of 2.02 g (1.0 eq.) sebacic acid and 3 g (2.5 eq.) poly(4-vinylpyridine) in 20 ml chloroform. After 3 hours at 25° C., the insoluble PVP.HCl was removed by filtration. The filtrate was quenched in 100 ml petroleum ether. The precipitated polymer was isolated by filtration, washed with anhydrous diethyl ether and dried for 24 hours at 40° C. in a vacuum oven.

A comparison of the purity of p(SA) synthesized using soluble and insoluble amines, TEA and PVP, respectively, with diphosgene or sebacoyl chloride as coupling agents, as shown in Table III, demonstrates that when soluble base, TEA, was used as an acid acceptor, the polymer contains a significant amount of TEA.HCl salt. The ratio of the salt to the polymer was 4:1 and 2:1 for the coupling agents diphosgene and sebacoyl chloride, respectively. When PVP, an insoluble acid acceptor, was used p(SA) of greater than 99.7% purity was obtained for both coupling agents.

PVP has another advantage besides high purity of the end product. It can be regenerated by neutralization with a sodium bicarbonate solution. Recycled PVP has a similar activity to that of the original PVP as an acid acceptor and forms a polyanhydride identical to the original polyanhydrides.

TABLE III

Presence of Amine hydrochloride in Solution Polymerized pSA as a Function of the Acid Acceptor.

| Polymerization Method[a] | Yield (%)[e] | IR[b] | TEA:PSA $^1$H NMR[c]/Elemental | GPC[d] | mp (°C.) | Elemental (% N, % Cl) |
|---|---|---|---|---|---|---|
| 1. A | [f] | + | 4.3:1/3.5:1 | + | 70–185[g] | 7.21, 19.63 |
| 2. B | 62 | — | — | — | 81–82 | 0.18, <0.10 |
| 3. C | [f] | + | 1.9:1/2.4:1 | + | 68–185[g] | 5.26, 13.14 |
| 4. D | 65 | — | — | — | 81–83 | 0.11, 0.027 |
| 5. E | 60 | — | — | — | 81–83 | 0.11, 0.015 |

[a]A is TEA/diphosgene; B is PVP/diphosgene; C is TEA/sebacoyl chloride; D is PVP/sebacoyl chloride, E is regenerated PVP/diphosgene.
[b]Typical absorbance of TEA-HCL follows (film cast); 2740 (w), 2600 (s, broad), 2530 (w, sharp), 2500 (s, sharp) cm$^{-1}$.
[c]H NMR of TEA-HCl (CDCl$_3$): 3.11 (q,2,J = 7.3 Hz), 1.42 (t, 3, J = 7.3 Hz); $^1$H-NMR of PSA (CDCl$_3$): 2.45 (t, 4, J = 7.3 Hz), 1.66 (br t, 4, J = 7.3 Hz), 1.33 (br s, 8).
[d]Sharp peak at Rt = 12.3 min.
[e]Pure poly(sebacic anhydride)
[f]Yield cannot be determined due to the presence of TEA.HCl.
[g]m.p. of TEA.HCl is 261° C.

Attempted purification of polymers synthesized with TEA as the acid acceptor using rapid water extraction results in a decrease in molecular weight and hydrolysis, as evidenced by GPC and IR spectra. The IR spectra of the polymer before and after purification reveals the disappearance of the amine salt (2740–2500 cm$^{-1}$). The IR spectra of polyanhydrides prepared with PVP as an acid acceptor reveals pure unhydrolyzed polymer.

EXAMPLE 4

Solution Polymerization of an Insoluble Polyanhydride with a soluble Acid Acceptor Insoluble polyanhydrides, poly(1,3-bis(p-carboxyphenoxy)propane) and poly(terephthalic anhydride), were polymerized as above but using only soluble amines such as TEA or pyridine as the acid acceptors. The polymers precipitated during the reaction and were isolated by filtration. The results are shown in Table IV.

TABLE IV

Solution Polymenzation of Insoluble Polymers Using Phosgene and Diphosgene as Coupling Agents.

| | Acid[c] | Coupling Agent[b] | Acid Acceptor[c] | Molecular Weight Mw | Mn | IR (cm$^{-1}$) | | MP (°C.) |
|---|---|---|---|---|---|---|---|---|
| 1. | Adipic acid | P | TEA | 7600 | 3350 | 1820 | 1735 | 70–73 |
| 2. | " | P | PVP | 8300 | 3600 | 1810 | 1740 | 70–74 |
| 3. | " | D | TEA | 6900 | 3200 | 1820 | 1740 | 69–73 |
| 4. | Dodecanoic acid | P | TEA | 14100 | 6500 | 1810 | 1740 | 92–95 |
| 5. | Dodecanoic acid | P | PVP | 12600 | 5900 | 1810 | 1740 | 90–95 |
| 6. | Dodecanoic acid | D | PVP | 13750 | 4800 | 1805 | 1740 | 92–94 |
| 7. | Terephthalic acid[a] | P | TEA | — | — | 1780 | 1735 | >300 |
| 8. | Terephthalic acid[a] | P | Pyridine | — | — | 1780 | 1735 | >300 |
| 9. | Therphthalic acid[a] | D | TEA | — | — | 1780 | 1730 | >300 |
| 10. | PDP | P | TEA | 8400 | 3650 | 1800 | 1735 | 98–101 |
| 11. | " | P | PVP | 7950 | 2100 | 1805 | 1740 | 100–102 |
| 12. | " | D | TEA | 9200 | 2350 | 1805 | 1735 | 98–102 |
| 13. | CPP[a] | P | TEA | — | — | 1780 | 1730 | 262–265 |
| 14. | " | P | TEA | — | — | 1780 | 1735 | 265–266 |
| 15. | " | D | TEA | — | — | 1780 | 1735 | 264–266 |
| 16. | PHE—GLU | D | TEA | 7500 | 2800 | 1800 | 1740 | — |

TABLE IV-continued
Solution Polymerization of Insoluble Polymers Using Phosgene and Diphosgene as Coupling Agents.

| | Acid[c] | Coupling Agent[b] | Acid Acceptor[c] | Molecular Weight Mw | Mn | IR (cm$^{-1}$) | | MP (°C.) |
|---|---|---|---|---|---|---|---|---|
| 17. | " | D | PVP | 4680 | 2400 | 1800 | 1740 | — |

[a]P is phosgene solution, D is diphosgene,
[b]Polymers are insoluble
[c]PDP is phenylenedipropionic acid, CPP is 1,3-bis(p-carboxyphenoxy)propane, GLU-PHE is N-carbobenzoxy-L-phenylalanyl-L-glutamic acid.

Isolation of the polymer using an insoluble acid acceptor is preferred over the two phase solvent separation method since high boiling point solvents such as DMF or toluene do not have to be removed at ambient temperature to avoid decomposition of the formed polyanhydride. In contrast to the traditional use of dehydration agents, the use of insoluble acid acceptors such as poly(4-vinylpyridine) or inorganic bases yield highly pure polymers. The use of various solvent systems is complementary to the use of the insoluble bases in chloroform. The choice of the right solvent system can be used to precipitate exclusively either the polymer or the amine-acid salt, using filtration to yield pure polymers. These methods are advantageous for the polymerization of heat sensitive dicarboxylic acids such as therapeutically active diacids and polyanhydrides of dipeptides.

Figure 2:
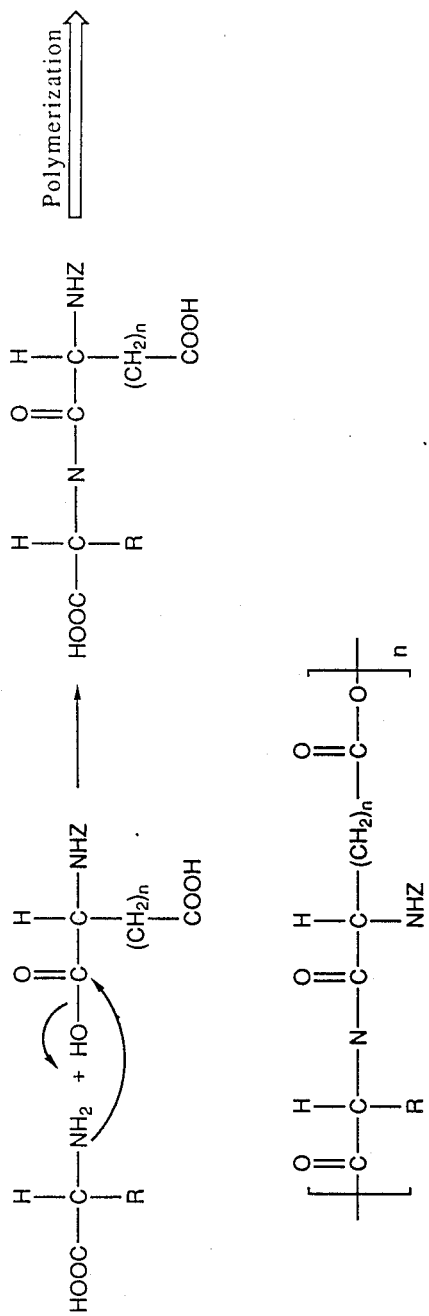
FIG. 2 is the formation of polyanhydrides from dipeptides containing glutamic or aspartic acid which are polymerized using a coupling agent and a removable acid acceptor.

EXAMPLE 5
Solution Polymerization of Polyanhydrides from Dipeptides of Aspartic or Glutamic Acid Polyanhydrides formed of dipeptides of an amino acid and either glutamic acid or aspartic acid can be prepared using the present method. For example, as shown in FIG. 2, phenylalanine-Z-glutamic acid or phenylalanine-Z-aspartic acid can be prepared. Z represents a protecting group.

The starting material, N-carbobenzoxy-L-phenylalanyl-L-glutamic acid, for the synthesis of poly(N-carbobenzoxy-DL-phenylalanine glutamic) anhydride, was synthesized according to *The Practice of Peptide Synthesis*, Bodansky, et al., Editors (Springer-Berlag, New York 1984). One gram monomer (2.5 mmol) was dissolved in a solution of 0.51 g TEA (5 mmol) in 10 ml chloroform, followed by the slow addition of 1.25 mmol disphosgene over 15 minutes. The resulting polyanhydride was isolated and purified. The analysis is shown as part of in Table IV.

The present invention has been described with respect to specific embodiments. Variations and modifications of the method for synthesizing polyanhydrides using a coupling agent and an insoluble acid acceptor or two phase solvent separation will be obvious to those skilled in the arts in the foregoing detailed description. Such modifications and variations are intended to come within the scope of the appended claims.

We claim:

1. A highly pure polyanhydride produced by reacting a dicarboxylic acid with phosgene or diphosgene in the presence of an acid acceptor and in a solvent to produce a polyanhydride soluble in said solvent and byproduct acid acceptor insoluble in said solvent, and removing insoluble byproduct acid acceptor and any unreacted phosgene or diphosgene, said polyanhydride consisting essentially of polyanhydride.

2. The highly pure polyanhydride of claim 1 wherein the insoluble acid acceptor is selected from the group consisting of insoluble polyamines, crosslinked polyamines, and inorganic bases.

3. The highly pure polyanhydride of claim 2 wherein the acid acceptor is selected from the group consisting of $K_2CO_3$, $Na_2CO_3$, $NAHCO_3$, $CaCO_3$, poly(4-vinylpyridine) and polyethyleneimine.

4. A method for preparing highly pure polyanhydride comprising reacting a dicarboxylic acid with phosgene or diphosgene in the presence of an acid acceptor and in a solvent to produce a polyanhydride and byproduct acid acceptor insoluble in said solvent, and removing insoluble byproduct acid acceptor and any unreacted phosgene or diphosgene from said polyanhydride.

5. The method of claim 4 wherein the insoluble acid acceptor is selected from the group consisting of insoluble polyamines, crosslinked polyamines, and inorganic bases.

6. The method of claim 5 wherein the insoluble acid acceptor is selected from the group consisting of polyethyleneimine, poly(4-vinylpyridine), $K_2CO_3$, $Na_2CO_3$, $NaHCO_3$, and $CaCO_3$.

* * * * *

UNITED STATES PATENT AND TRADEMARK OFFICE
CERTIFICATE OF CORRECTION

PATENT NO. : 4,916,204
DATED : April 10, 1990
INVENTOR(S) : Abraham J. Domb, Robert S. Langer, Eyal Ron, Steven Giannos, Rohit Kothari, Edith Mathiowitz It is certified that error appears in the above-identified patent and that said Letters Patent is hereby corrected as shown below:

Column 1, line 66, replace "oxazoidinyl" with --oxazolidinyl--.
Column 3, line 53, replace "disphosgene" with --diphosgene--.
Column 6, line 13, replace "cloroform" with --chloroform--.
Column 7, lines 5 and 6, replace "disphosgene" with -- diphosgene--.
Column 9, line 43, replace "Bodansky" with --Bodanszky--.
Column 9, line 47, replace "disphosgene" with --diphosgene--.

Signed and Sealed this

Thirty-first Day of May, 1994

Attest:

BRUCE LEHMAN

Attesting Officer   Commissioner of Patents and Trademarks